US008879064B2

(12) United States Patent
O'Connor et al.

(10) Patent No.: US 8,879,064 B2
(45) Date of Patent: Nov. 4, 2014

(54) APPARATUS AND METHOD FOR TRANSPORTING AN AEROSOL

(75) Inventors: Ciaran John Patrick O'Connor, Bozeman, MT (US); Shane Hilliard, Bozeman, MT (US)

(73) Assignee: Electro Scientific Industries, Inc., Portland, OR (US)

( * ) Notice: Subject to any disclaimer, the term of this patent is extended or adjusted under 35 U.S.C. 154(b) by 426 days.

(21) Appl. No.: 13/336,991

(22) Filed: Dec. 23, 2011

(65) Prior Publication Data

US 2013/0162991 A1 Jun. 27, 2013

(51) Int. Cl.

*G01N 21/00* (2006.01)
*G01N 21/84* (2006.01)
*G01N 1/22* (2006.01)

(52) U.S. Cl.

CPC . *G01N 1/22* (2013.01); *G01N 21/84* (2013.01)
USPC ............................ 356/432; 356/436; 356/437

(58) Field of Classification Search

CPC ....... G01N 21/01; G01N 21/84; G01N 21/22; G01J 3/443
See application file for complete search history.

(56) References Cited

U.S. PATENT DOCUMENTS

| | | | | |
|---|---|---|---|---|
| 4,206,160 | A * | 6/1980 | Suddendorf et al. | 261/78.2 |
| 4,600,608 | A * | 7/1986 | Ankrett | 427/424 |
| 6,342,397 | B1 * | 1/2002 | Soini et al. | 436/518 |
| 6,873,419 | B2 | 3/2005 | Detalle et al. | |
| 2003/0095266 | A1 | 5/2003 | Detalle et al. | |
| 2005/0061779 | A1 | 3/2005 | Blumenfeld et al. | |
| 2005/0264815 | A1 * | 12/2005 | Wechsler et al. | 356/440 |
| 2007/0046934 | A1 | 3/2007 | Roy | |
| 2009/0095128 | A1 * | 4/2009 | Frey et al. | 75/338 |
| 2009/0273782 | A1 | 11/2009 | Yoo et al. | |
| 2010/0252731 | A1 | 10/2010 | Reilly | |
| 2010/0300221 | A1 | 12/2010 | Lee et al. | |
| 2012/0074307 | A1 * | 3/2012 | Becker et al. | 250/282 |

FOREIGN PATENT DOCUMENTS

| | | | |
|---|---|---|---|
| DE | 19838383 | A1 | 3/2000 |
| DE | 19838383 | C2 | 10/2001 |
| JP | 2003270208 | A | 9/2003 |
| JP | 200425390 | A | 11/2004 |
| JP | 2005106688 | A | 4/2005 |
| JP | 2006153743 | A | 6/2006 |
| JP | 2006184111 | A | 7/2006 |
| JP | 2007322226 | A | 12/2007 |
| JP | 04038506 | B2 | 1/2008 |
| JP | 2008008866 | A | 1/2008 |
| JP | 04180434 | B2 | 11/2008 |
| JP | 04470908 | B2 | 6/2010 |
| WO | WO2009/137494 | A1 | 11/2009 |
| WO | WO 2011/006156 | A2 | 1/2011 |

OTHER PUBLICATIONS

Overview Laser-ablation Mass Spectrometry, 1 page, retrieved from www.rhul.ac.uk/earthsciences/labs/laicpms.aspx on Dec. 6, 2011.
Clifford Gabay, "Resonetics Resolution Product Line of Laser Ablation Instruments", 23 pages, Jul. 1, 2009, retrieved from www.resonetics.com/pdfs/resonetics_product_line.pdf on Dec. 6, 2011.
Sample Introduction Systems Solid-Laser Ablation-II, 43 pages, retrieved from www.nd.edu/~asimonet/ENGV60500/Lecture_6_09_20_2011.pdf on Dec. 6, 2011.
International Search Report of PCT/US2012/063097, 2 pages, 2013.
Written Opinion of PCT/US2012/063097, 2 pages, 2013.

* cited by examiner

*Primary Examiner* — Tarifur Chowdhury
*Assistant Examiner* — Hina F Ayub
(74) *Attorney, Agent, or Firm* — Haynes Beffel & Wolfeld LLP

(57) ABSTRACT

An apparatus can include ablation chamber body having a transmission window and defining an accommodation region configured to accommodate a target that is movable relative to the transmission window. An aerosol transmission conduit is configured to transport an aerosol produced within the accommodation region to a sample receiving region of an analysis system along a substantially straight transport path.

26 Claims, 2 Drawing Sheets

APPARATUS AND METHOD FOR TRANSPORTING AN AEROSOL

BACKGROUND

Embodiments of the present invention as exemplarily described herein relate generally to apparatuses for providing aerosol samples and to methods of providing aerosol samples. More particularly, embodiments of the present invention relate to apparatuses and methods capable of transporting aerosol samples to an analysis system with increased efficiency and reduced fractionation.

Analysis systems, such as mass spectrometry (MS) systems, optical emission spectrometry (OES) systems and the like, can be used to analyze the composition of a target material. Often, a sample of the target material is provided to an analysis system in the form of an aerosol. As is known in the art, an aerosol generally characterized as a colloid suspension of solid and possibly liquid particles in a gas. The aerosol is typically produced by an aerosol producing apparatus, entrained by a flowing carrier gas and transported to the analysis system as a sample via an aerosol transport conduit. Conventional aerosol transport conduits can be bent to enable the aerosol producing apparatus to produce multiple samples from different locations of a target material to be analyzed at an analysis system. Thus, aerosol transport paths defined by conventional aerosol transport conduits are non-linear. Due to the non-linearity of conventional aerosol transport paths, the aerosol experiences fractionation as it is transported from the aerosol producing apparatus to the analysis system. As is known in the art, fractionation occurs when particles of different elements, isotopes, size and/or geometry within the aerosol become centrifugally separated as the direction along the aerosol transport path changes. Due to the effects of fractionation, the compositional analysis performed by the analysis system may not accurately correspond to the actual composition of the aerosol produced by the aerosol producing apparatus. Bends within conventional aerosol transport paths can also cause the aerosol transport velocity to vary along the length of the transport path and also vary at different locations within the aerosol transport conduit adjacent to a bend. Such non-uniform transport velocities can cause, among other deleterious effects, agglomeration of particles within the aerosol. As a result, relatively small particles within the aerosol undesirably agglomerate to form larger particles, which tends to decrease the overall transport efficiency of the aerosol along the along the aerosol transport path.

Conventional aerosol transport conduits can also be made flexible to enable the aerosol producing apparatus to produce multiple samples from different locations of a target material to be analyzed at an analysis system. However using flexible aerosol transport conduits can cause the compositional analysis performed by the analysis system to undesirably change depending on the location of the target material from which the aerosol was generated. To reduce undesirable variability of compositional analyses induced by a flexible aerosol transport conduit, the flexible aerosol transport conduit is generally provided as tube roughly a few meters in length. Thus, any movement between opposite ends of the flexible aerosol transport conduit result in a reduced amount of bending between the opposite ends of the flexible aerosol transport conduit. Due to the relatively long length of such aerosol transport conduits, however, the aerosol transport time within the conduit can be undesirably increased. As a result, relatively small particles within the aerosol undesirably agglomerate in a similar manner as described above.

In addition, flexible or bent aerosol transport conduits are conventionally made of a plastic material that can be permeable to atmospheric gases. As a result, atmospheric gases can become undesirably entrained with the aerosol as it is transported through the aerosol transport conduit and cause problems with compositional analysis of the aerosol (e.g., due to formation of interferences and high backgrounds).

SUMMARY

In one embodiment, an apparatus may be provided with a first chamber body having a transmission window configured to transmit a radiation pulse along a transmission direction, the radiation pulse having a fluence sufficient to ablate a portion of a target; a second chamber body adjacent to the first chamber body, wherein the second chamber body is configured to support a target that is ablatable by the radiation pulse and wherein the second chamber body is moveable relative to the transmission window along a translation direction different from the transmission direction, wherein the first chamber body and the second chamber body at least partially define an accommodation region within which the target can be accommodated; and an aerosol transport conduit having a first end and a second end opposite the first end, the aerosol transport conduit defining an aerosol transport region in fluid communication with the accommodation region at the first end and in fluid communication with a region outside the accommodation region at the second end, wherein the aerosol transport conduit is configured to transport an aerosol along a substantially straight transport path extending from the end to the second end, the aerosol including a material ablatable from the target.

In another embodiment, an apparatus may be provided with an ablation chamber including a transmission window and an accommodation region, wherein the transmission window is configured to transmit a radiation pulse along a transmission direction, the radiation pulse having a fluence sufficient to ablate a portion of a target, and wherein the accommodation region is configured to accommodate a target; a target holder disposed within the accommodation region and configured to support the target within the accommodation region, wherein the target holder is configured such that at least one of a position and an orientation of the target within the accommodation region is adjustable; and an aerosol transport conduit having a first end and a second end opposite the first end, the aerosol transport conduit defining an aerosol transport region in fluid communication at the first end and in fluid communication with a region outside the accommodation region at the second end, wherein the aerosol transport conduit is configured to transport an aerosol along a substantially straight transport path extending from the end to the second end, the aerosol including a material ablatable from the target.

In another embodiment of the present invention, a method may include transporting an aerosol from an accommodation region of an ablation chamber body to a sample receiving region of an analysis system along a substantially straight transport path, wherein the analysis system is configured to perform a compositional analysis of the aerosol received within the sample receiving region.

DETAILED DESCRIPTION OF THE ILLUSTRATED EMBODIMENTS

Figure 1:
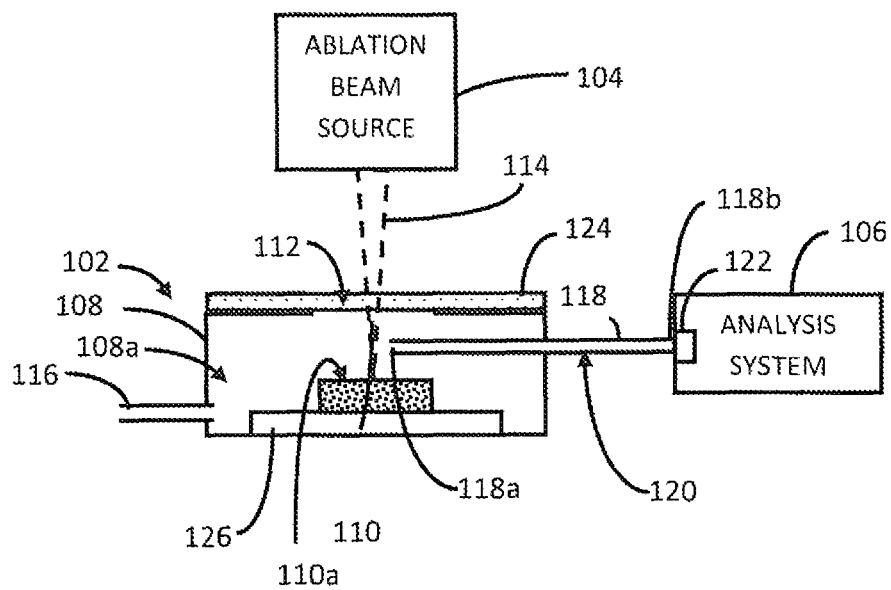
FIG. 1 is a schematic view illustrating an apparatus according to one embodiment.

The invention is described more fully hereinafter with reference to the accompanying drawings, in which example embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the sizes and relative sizes of layers and regions may be exaggerated for clarity.

It will be understood that, although the terms first, second, third, etc., may be used herein to describe various elements, components, regions, sets, etc., these elements, components, regions, sets, should not be limited by these terms. These terms are only used to distinguish one element, component, region, set, etc., from another element, component, region, set, etc. Thus, a first element, component, region, set, etc., discussed below could be termed a second element, component, region, set, etc., without departing from the teachings provided herein.

The terminology used herein is for the purpose of describing particular example embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

FIG. 1 is a schematic view illustrating an apparatus according to one embodiment.

Referring to FIG. 1, an apparatus, such as apparatus 100, includes an ablation chamber 102, an ablation beam source 104, and an analysis system 106. In other embodiments, however, one or both of the ablation beam source 104 and the analysis system 106 may be omitted from the apparatus 100.

As exemplarily illustrated, the ablation chamber 102 includes an ablation chamber body 108 defining an accommodation region 108a configured to accommodate a target 110, a transmission window 112 configured to transmit a radiation pulse 114 along a transmission direction, a carrier gas inlet 116 configured to transmit a carrier gas (e.g., helium, argon, or the like or a combination thereof) from a carrier gas source (not shown) outside the ablation chamber 102 into the accommodation region 108a, and an aerosol transport conduit 118 coupled to the ablation chamber body 108. As will be discussed in greater detail below, the radiation pulse 114 has a fluence sufficient to ablate a portion of the target 110, thereby producing an aerosol plume (also referred to herein simply as an "aerosol," a "plume", a "plume of aerosol", or the like) including material ablated from the target entrained in the carrier gas.

The aerosol transport conduit 118 includes a first end 118a and a second end 118b and defines an aerosol transport region 120 extending from the first end 118a to the second end 118b. In the illustrated embodiment, the aerosol transport conduit 118 is configured such that the first end 118a extends into the accommodation region 108a and the second end extends outside the ablation chamber body 108. In another embodiment, however, the aerosol transport conduit 118 can be configured such that the first end 118a does not extend into the accommodation region 108a. Likewise, the aerosol transport conduit 118 can be configured such that the second end 118b does not extend outside the ablation chamber body 108. The aerosol transport region 120 defines a transport path along which an aerosol is transportable. As exemplarily illustrated, the aerosol transport region 120 is in fluid communication with the accommodation region 108a at the first end 118a and is in fluid communication with a region outside accommodation region 108a (e.g., a sample receiving region 122 of the analysis system 106) at the second end 118b. Constructed as described above, the aerosol transport conduit 118 is configured to receive a plume of aerosol produced within the accommodation region 108a and transport the plume of aerosol within the aerosol transport region 120, along the transport path, to the sample receiving region 122 of the analysis system 106. As will be discussed in greater detail below, the analysis system 106 is configured to perform a compositional analysis on the aerosol transported by the aerosol transport conduit 118.

In one embodiment, the transport path defined by the aerosol transport region 120 is substantially straight such that the aerosol undergoes no fractionation, or no detectable fractionation (i.e., "substantially no fractionation"), as the aerosol is transported from the accommodation region 108a to the sample receiving region 122 (i.e., from the first end 118a to the second end 118b). In another embodiment, the transport path defined by the aerosol transport region 120 is substantially straight such that the transport velocity of the aerosol is substantially constant as the aerosol is transported from the accommodation region 108a to the sample receiving region 122 (i.e., from the first end 118a to the second end 118b).

In one embodiment, the aerosol transport conduit 118 is substantially rigid such that the transport path can remain substantially straight under normal operating conditions during which the aerosol is transported from the first end 118a to the second end 118b. Because the aerosol transport conduit 118 is substantially rigid, it can be formed of a metallic material (e.g., stainless steel, or the like). In one embodiment, the metallic material can be a material that is impermeable to atmospheric gases, or that is less permeable to atmospheric gases than plastic material from which the aforementioned conventional aerosol transport conduits are formed.

The length of the aerosol transport conduit 118, measured along the transport path from the first end 118 to the second end 118b, may be less than 5 meter (m). In one embodiment, the length of the aerosol transport conduit 118 is less than 1 m. In another embodiment, the length of the aerosol transport conduit 118 is less than 10 centimeters (cm). In yet another embodiment, the length of the aerosol transport conduit 118 is less than 5 cm. In still another embodiment, the length of the aerosol transport conduit 118 is less than 3 cm. In such embodiments, however, the length of the aerosol transport conduit 118 can generally be greater than 1 cm, but may be less than 1 cm. In some embodiments, the length of the aerosol transport conduit 118 can be selected to prevent or otherwise reduce the degree to which particles within the aerosol undesirably agglomerate as the aerosol is transported from the accommodation region 108*a* to the sample receiving region 122 (i.e., from the first end 118*a* to the second end 118*b*). Selection of the length of the aerosol transport conduit 118 can be affected by one or more factors such as the material from which the target 110 is formed, the energy density of the radiation pulse 114, the pulse width of the radiation pulse 114, the wavelength of the radiation pulse 114, the carrier gas flow rate, or the like.

The aerosol transport conduit 118 is coupled to the ablation chamber body 108 so as to be fixedly situated relative to the transmission window 112. In one embodiment, the aerosol transport conduit 118 is fixedly situated relative to the transmission window 112 such that the aerosol transport conduit 118 is positionally fixed relative to the transmission window 112. In another embodiment, the aerosol transport conduit 118 is fixedly situated relative to the transmission window 112 such that the aerosol transport conduit 118 is orientationally fixed relative to the transmission window 112.

The ablation beam source 104 is configured to direct the radiation pulse 114 into the accommodation region 108*a*. In another embodiment, the ablation beam source 104 is also configured to generate the radiation pulse 114. Although not illustrated, the ablation beam source 104 may include a radiation source such as one or more lasers configured to generate a beam of one or more pulses of laser radiation. The one or more lasers may each be, configured to generate laser radiation having a wavelength greater than about 157 nm and less than about 1064 nm. For example, the one or more lasers may each be configured to generate a wavelength selected from the group consisting of 266 nm, 213 nm, 193 nm, or the like. Each of the one or more lasers may be configured to generate laser pulses having pulse width between about 1.0 picoseconds to about 25 nanoseconds. The ablation beam source 104 may also include laser optics configured to focus the laser radiation generated by one or more of the lasers.

As mentioned above, the analysis system 106 is configured to perform a compositional analysis on the aerosol transported by the aerosol transport conduit 118. The analysis system 106 may be provided as any suitable system such as an MS system (e.g., a noble gas MS system, a stable isotope MS system, etc.), an OES system, or the like, or a combination thereof. Generally, however, the analysis system 106 includes a sample preparation module configured to excite (e.g., ionize, atomize, illuminate, heat, etc.) one or more components of the aerosol received within the sample, receiving region 122 and a detector module configured to detect one or more characteristics (e.g., electromagnetic emission or absorption, particle mass, ionic mass, or the like or a combination thereof) of the excited component(s) of the aerosol received in the sample receiving region 122. Techniques for exciting one or more components of the aerosol received within the sample receiving region 122 include plasma generation (e.g., via an inductively coupled plasma (ICP) torch), spark ionization, thermal ionization, atmospheric pressure chemical ionization, fast atom bombardment, glow discharge, and the like or a combination thereof. In one embodiment, the analysis system 106 may further include a sort module configured to sort the excited component(s) of the aerosol received in the sample receiving region 122 based on one or more of the aforementioned characteristics before the detector module detects a characteristic.

In one embodiment, the apparatus 100 further includes a shield 124 disposed between the ablation chamber 102 and the ablation beam source 104. The shield 124 may be formed of a material that is at least partially transparent to the radiation pulse 114. In the illustrated embodiment, the shield 124 abuts the ablation chamber body 108 and covers the transmission window 112 to prevent debris (e.g., dust, water vapor, atmospheric gases such as air, and the like) from undesirably entering into the accommodation region 108*a* during ablation of the target 110. The ablation beam source 106 is generally disposed in close proximity to the shield 124 (as illustrated), and may abut the shield 124, to reduce or eliminate any deleterious interference of transmission of the radiation pulse into the accommodation region 108*a* caused by debris outside the ablation chamber body 108. In one embodiment, the shield 124 may be coupled to one or both of the ablation beam source 104 and the ablation chamber body 108.

In another embodiment, the apparatus 100 optionally includes a target holder 126 disposed within the accommodation region 108*a*. The target holder 126 may be configured to hold or support the target 110 within the accommodation region to ensure that a surface 110*a* of the target 110 is desirably situated within the accommodation region 108*a* when the radiation pulse 114 is transmitted into the accommodation region 108*a*. In one embodiment, the target holder 126 may be configured such that at least one of a position and an orientation of the target 110 within the accommodation region 108 is adjustable to ensure that the portion of the surface 110*a* to be ablated by the radiation pulse 114 is desirably situated within the accommodation region 108*a*, even if other portions of the surface 110*a* are not desirably situated within the accommodation region 108*a*.

FIG. 2 is a cross-sectional view schematically illustrating one embodiment of an ablation chamber of the apparatus shown in FIG. 1. FIG. 3 is a cross-sectional view schematically illustrating an embodiment in which the second chamber body of the ablation chamber shown in FIG. 2 is moveable relative to the first chamber body.

Referring to FIG. 2, the ablation chamber body 108 shown in FIG. 1 may, according to one embodiment, include a first chamber body 202 and a second chamber body 204 adjacent to the first chamber body 202. As exemplarily shown, the first chamber body 202 and the second chamber body 204 define the accommodation region 108*a*. However, the ablation chamber 102 may include other components that at least partially define the accommodation region 108*a*. Thus, the first chamber body 202 and the second chamber body 204 may at least partially define the accommodation region 108*a*. Although not shown, one or more biasing members (e.g., springs) may be provided to uniformly press the one chamber body (e.g., the second chamber body 204) against the other chamber body (e.g., the first chamber body 202).

The transmission window 112 is defined within the first chamber body 202 and the second chamber body 204 is moveable relative to the transmission window 112 (e.g., as indicated by arrow 302 shown in FIG. 3). For example, the second chamber body 204 may be placed on movable stage 206 (e.g., supported by a relatively stationary base 208) that is configured to move the second chamber body 204 along one or more translation directions different from the aforementioned transmission direction. The base 208 may, in turn, be provided on a sufficiently stable mounting surface (not shown) such as a table, a floor, or the like. A frame (not shown) supported by, for example, the aforementioned mounting surface, may be coupled to the first chamber body 202 to support the first chamber body 202 as the second chamber body 204 is moved by the movable stage 206. In one embodiment in which the shield 124 is coupled to one or both of the ablation beam source 104 and the ablation chamber body 108, the frame may be similarly coupled to one or more of the shield 124 and the ablation beam source 104 in addition to (or instead of) the first chamber body 202.

In the illustrated embodiment, the aerosol transport conduit 118 is extends through the first chamber body 202 such that the first end 118a extends into the accommodation region 108a and the second end extends outside the ablation chamber body 108. In other embodiments, however, the one or both of the first end 118a and the second end 118b are disposed at within the first chamber body 202 or at an edge of the first chamber body 202. Moreover, aerosol transport conduit 118 may be provided as a bore or one, or more channels (not shown) formed in the first chamber body 202.

The aerosol transport conduit 118 can be coupled to the first chamber body 202 in any suitable manner that results in the aerosol transport conduit 118 being fixedly situated relative to the transmission window 112 as described above. For example, the aerosol transport conduit 118 may be inserted into a bore (not shown) or one or more channels (not shown) formed in the first chamber body 202 and secured therein by an adhesive, one or more welds, or other locking members (e.g., screws, clamps, or the like or a combination thereof) or any biasing member structured to bias the aerosol transport conduit 118 against the first chamber body 202. In one embodiment, the aerosol transport conduit 118 is coupled to the first chamber body 202 such the aerosol transport conduit 118 is fixedly situated relative to the transmission window 112 as the second chamber body 204 moves relative to the transmission window 112.

In one embodiment, the ablation chamber 102 may include an aerosol collector 210 defining a collection region 210a. In one embodiment, the aerosol collector 210 is coupled to the first chamber body 202 by a collector support member 212 (e.g., a pin, screw, clamp, etc.). The collector support member 212 can be configured to align the aerosol collector 210 relative to the transmission window 112 to ensure that the radiation pulse 114 is transmitted into the accommodation region 108a through the collection region 210a with little or no interference by the aerosol collector 210. In one embodiment, collector support member 212 may be configured such that at least one of a position and an orientation of the aerosol collector 210 is adjustable relative to the transmission window 112.

At least a portion of the aerosol collector 210 can be disposed within the accommodation region 108a such that the collection region 210a is in fluid communication with the accommodation region 108a. In one embodiment, the aerosol collector 210 is disposed such that a small gap is formed between the aerosol collector 210 and the surface 110a of the target 110. The height of the gap should be selected to ensure that at least a portion of the aerosol plume produced upon ablation of the surface 110a by the radiation pulse 114 is formed within the collection region 110a. The height of the gap can also be selected so as to ensure that carrier gas flowing into the accommodation region 108a and over the surface 110a of the target 110 can flow into the collection region 210a.

At least a portion of the aerosol collector 210 can be disposed within the accommodation region 108a such that the collection region 210a is in fluid communication with the aerosol transport region 120. In the illustrated embodiment, the aerosol collector 210 includes a bore (shown, but not labeled) located between the bottom and the top of the aerosol collector 210. The bore may be in fluid communication with the collection region 210a and the first end 118a of the aerosol transport conduit 118 can be inserted into or otherwise coupled to the bore. In other embodiments, however, the first end may be disposed above the top of the aerosol collector 210.

By providing the aerosol collector 210 as exemplarily described above, the volume of the aerosol plume produced upon ablation of the surface 110a by the radiation pulse 114 can be made relatively small, thereby improving transport of the aerosol through the aerosol transport region 120 to the sample receiving region 122 of the analysis system 106. While the aerosol collector 210 has been described above as a separate piece from the first chamber body 202, the aerosol collector 210 and the first chamber body 202 can also be formed as a single, monolithic structure.

Figure 2:
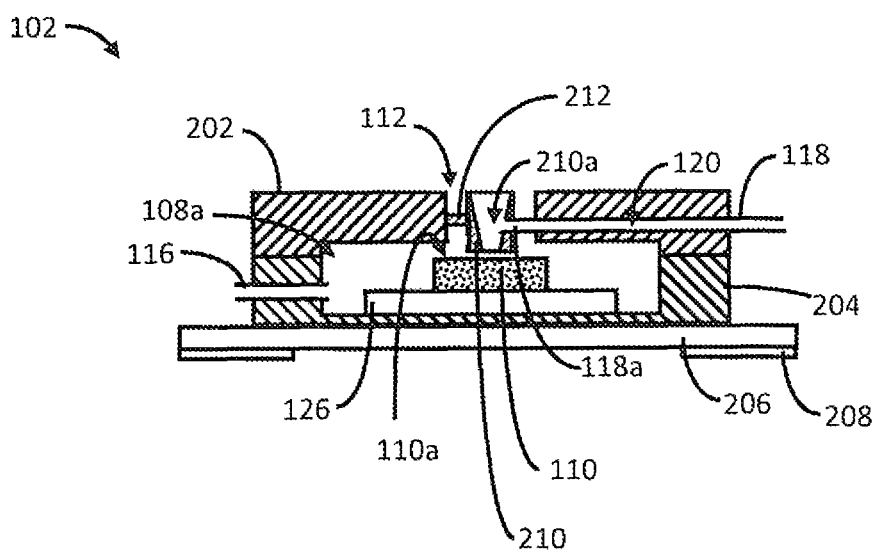
FIG. 2 is a cross-sectional view schematically illustrating one embodiment of an ablation chamber of the apparatus shown in FIG. 1.
Figure 3:
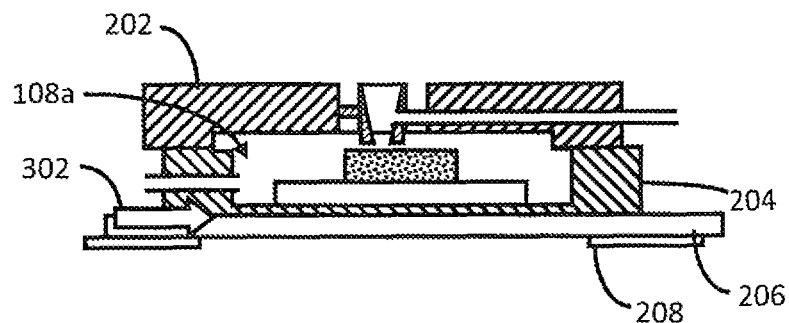
FIG. 3 is a cross-sectional view schematically illustrating an embodiment in which the second chamber body of the ablation chamber shown in FIG. 2 is moveable relative to the first chamber body.
Figure 4:
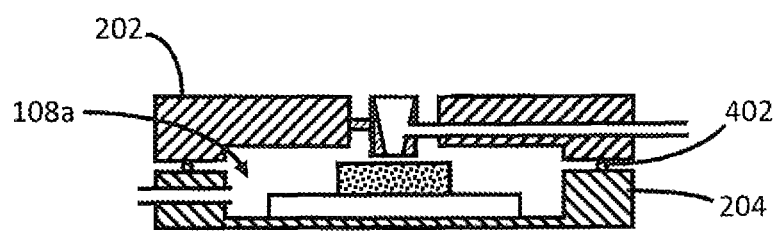
FIGS. 4 and 5 are cross-sectional views schematically illustrating barriers configured to prevent debris from entering into the ablation chamber shown in FIG. 2, according to some embodiments.
Figure 5:
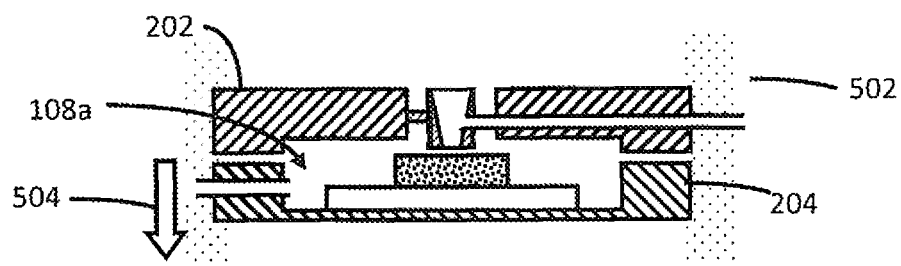

FIGS. 4 and 5 are cross-sectional views schematically illustrating barriers configured to prevent debris from entering into the ablation chamber shown in FIG. 2, according to some embodiments.

As discussed above, the second chamber body 204 is movable relative to the first chamber body 202 along one or more translation directions. In some embodiments, a barrier can be provided to prevent debris (e.g., dust, water vapor, atmospheric gases such as air, and the like) from undesirably entering into the accommodation region 108a when the second chamber body 204 is moved.

Referring to FIG. 4, a barrier according to one embodiment can be provided as a seal, such as seal 402, disposed between opposing surfaces of the first chamber body 202 and the second chamber body 204. The seal 402 can be provided as any type of seal capable of preventing debris from entering into the accommodation region 108a while permitting the second chamber body 204 from moving relative to the first chamber body 202 without generating an undesirable amount of friction. In one embodiment, the seal 402 is provided as a face seal (e.g., an O-ring, C-ring, U-ring, etc.). The face seal may optionally be spring loaded. An exterior surface of the face seal may be coated a relatively inert, low-friction material such as polytetrafluoroethylene (PTFE).

Referring to FIG. 5, a barrier according to another embodiment can be provided as a gas curtain, such as gas curtain 502, surrounding a perimeter of the first chamber body 202 and the second chamber body 204. The gas curtain 502 may include a curtain of gas (e.g., helium, argon, etc.) flowing (e.g., along the direction indicated by arrow 504) with at a sufficient flow rate to prevent debris from undesirably entering into the accommodation region 108a.

Although only two examples of barriers have been illustrated, it will be appreciated that other barriers may be provided. For example, a barrier could be provided as a bellows-type structure including a flexible sheet material (e.g., a fabric) coupled to the first chamber body 202 and the second chamber body 204 that changes shape as the second chamber body 204 moves relative to the first chamber body 202, but that maintains a suitable barrier between the accommodation region 108 and the environment outside the ablation chamber body 108. It will also be appreciated that more than one type of barrier can be simultaneously used to help prevent debris from undesirably entering into the accommodation region 108.

Having described the apparatus above, it will be appreciated that embodiments of the present invention may be implemented and practiced in many different forms. For example, in one embodiment, an apparatus may include an aerosol transmission conduit configured to transport an aerosol from an accommodation region of an ablation chamber body to a sample receiving region of an analysis system along a substantially straight transport path, wherein the analysis system is configured to perform a compositional analysis of the aerosol received within the sample receiving region.

In another embodiment of the present invention, an apparatus may include a first portion of an ablation chamber body and an aerosol transmission conduit, wherein the first portion of an ablation chamber body and the aerosol transmission conduit are configured to transport an aerosol from an accommodation region of an ablation chamber body to a sample receiving region of an analysis system along a substantially straight transport path while another portion of the ablation chamber body moves relative to the first portion of the ablation chamber body, wherein the analysis system is configured to perform a compositional analysis of the aerosol received within the sample receiving region.

In another embodiment of the present invention, a method may include transporting an aerosol from an accommodation region of an ablation chamber body to a sample receiving region of an analysis system along a substantially straight transport path, wherein the analysis system is configured to perform a compositional analysis of the aerosol received within the sample receiving region. In such an embodiment, the method may optionally include ablating a target within the accommodation region to produce the aerosol, performing the compositional analysis on the aerosol at the analysis system, or a combination thereof.

The foregoing is illustrative of embodiments of the invention and is not to be construed as limiting thereof. Although a few example embodiments of the invention have been described, those skilled in the art will readily appreciate that many modifications are possible in the example embodiments without materially departing from the novel teachings and advantages of the invention. Accordingly, all such modifications are intended to be included within the scope of the invention as defined in the claims. Therefore, it is to be understood that the foregoing is illustrative of the invention and is not to be construed as limited to the specific example embodiments of the invention disclosed, and that modifications to the disclosed example embodiments, as well as other embodiments, are intended to be included within the scope of the appended claims. The invention is defined by the following claims, with equivalents of the claims to be included therein.

What is claimed is:

1. An apparatus comprising:
    a first chamber body having a transmission window configured to transmit a radiation pulse along a transmission direction, the radiation pulse having a fluence sufficient to ablate a portion of a target;
    a second chamber body adjacent to the first chamber body, wherein the second chamber body is configured to support a target that is ablatable by the radiation pulse and wherein the second chamber body is moveable relative to the transmission window along a translation direction different from the transmission direction, wherein the first chamber body and the second chamber body at least partially define an accommodation region within which the target can be accommodated; and
    an aerosol transport conduit having a first end and a second end opposite the first end, the aerosol transport conduit defining an aerosol transport region in fluid communication with the accommodation region at the first end and in fluid communication with a region outside the accommodation region at the second end,
    wherein the aerosol transport conduit is configured to transport an aerosol along a substantially straight transport path extending from the first end to the second end, the aerosol including a material ablatable from the target.

2. The apparatus of claim 1, wherein the transport path is substantially straight such that the aerosol undergoes no fractionation or substantially no fractionation as it is transported from the first end to the second end.

3. The apparatus of claim 1, wherein the transport path is substantially straight such that the transport velocity of the aerosol is substantially constant as the aerosol is transported from the first end to the second end.

4. The apparatus of claim 1, wherein a length of the aerosol transport conduit from the first end to the second end is less than 3 m.

5. The apparatus of claim 4, wherein the length of the aerosol transport conduit from the first end to the second end is less than 1 m.

6. The apparatus of claim 5, wherein the length of the aerosol transport conduit from the first end to the second end is less than about 10 cm.

7. The apparatus of claim 6, wherein the length of the aerosol transport conduit from the first end to the second end is less than about 5 cm.

8. The apparatus of claim 1, wherein the aerosol transport conduit extends through the first chamber body.

9. The apparatus of claim 1, wherein the aerosol transport conduit is substantially rigid.

10. The apparatus of claim 1, wherein a portion of the aerosol transport conduit defining the aerosol transport region is metallic.

11. The apparatus of claim 1, wherein the aerosol transport conduit is orientationally fixed relative to the first chamber body.

12. The apparatus of claim 1, wherein the aerosol transport conduit is positionally fixed relative to the first chamber body.

13. The apparatus of claim 1, wherein the first end of the aerosol transport conduit extends into the accommodation region.

14. The apparatus of claim 1, wherein the second end of the aerosol transport conduit extends outside the accommodation region.

15. The apparatus of claim 1, wherein the first chamber body and the second chamber body are configured such that the target is moveable within the accommodation region relative to the transmission window.

16. The apparatus of claim 1, further comprising a barrier configured to prevent debris external to the ablation chamber from entering into the accommodation region.

17. The apparatus of claim 16, wherein the barrier comprises a seal located between the first chamber body and the second chamber body.

18. The apparatus of claim 16, wherein the barrier comprises a gas curtain surrounding a perimeter of the first chamber body and the second chamber body.

19. The apparatus of claim 1, further comprising an aerosol collector defining a collection region in fluid communication with the accommodation region and the aerosol transport region.

20. The apparatus of claim 1, further comprising a carrier gas inlet configured to transport a carrier gas from outside the accommodation region into the accommodation region.

21. The apparatus of claim 20, wherein the carrier gas inlet extends through the second chamber body.

22. The apparatus of claim 1, further comprising an ablation beam source adjacent to the transmission window, wherein the ablation beam source is configured to direct a pulse of radiation through the transmission window onto the target along the transmission direction, the radiation pulse having a fluence sufficient to ablate a portion of the target and produce the aerosol.

23. The apparatus of claim 1, further comprising an analysis system having a sample receiving region in fluid communication with the second end of the aerosol transport conduit such that the aerosol is receivable from the aerosol transport conduit within the sample receiving region as a sample, wherein the analysis system is configured to analyze a composition of the sample.

24. The apparatus of claim 23, wherein the aerosol transport conduit is configured to transport the aerosol along a substantially straight transport path extending from the accommodation region to the sample receiving region.

25. The system of claim 23, wherein the analysis system includes at least one selected from the group consisting of an optical emission spectrometry apparatus and a mass spectrometry apparatus.

26. An apparatus comprising:
  an ablation chamber including a transmission window and an accommodation region, wherein the transmission window is configured to transmit a radiation pulse along a transmission direction, the radiation pulse having a fluence sufficient to ablate a portion of a target, and wherein the accommodation region is configured to accommodate a target;
  a target holder disposed within the accommodation region and configured to support the target within the accommodation region, wherein the target holder is configured such that at least one of a position and an orientation of the target within the accommodation region is adjustable; and
  an aerosol transport conduit having a first end and a second end opposite the first end, the aerosol transport conduit defining an aerosol transport region in fluid communication at the first end and in fluid communication with a region outside the accommodation region at the second end,
  wherein the aerosol transport conduit is configured to transport an aerosol along a substantially straight transport path extending from the first end to the second end, the aerosol including a material ablatable from the target.

* * * * *